(12) United States Patent
Hamamoto et al.

(10) Patent No.: US 6,613,196 B2
(45) Date of Patent: Sep. 2, 2003

(54) METHOD FOR STOPPING PURIFYING COLUMN

(75) Inventors: Kei Hamamoto, Himeji (JP); Yukihiro Matsumoto, Kobe (JP); Sei Nakahara, Himeji (JP); Misao Inada, Himeji (JP)

(73) Assignee: Nippon Shokubai Co., Ltd. (JP)

( * ) Notice: Subject to any disclaimer, the term of this patent is extended or adjusted under 35 U.S.C. 154(b) by 0 days.

(21) Appl. No.: 09/901,267

(22) Filed: Jul. 9, 2001

(65) Prior Publication Data

US 2002/0027067 A1 Mar. 7, 2002

(30) Foreign Application Priority Data

Jul. 21, 2000 (JP) ........................... 2000-220735

(51) Int. Cl.$^7$ ............... B01D 3/42; C07C 51/44
(52) U.S. Cl. ............... 203/3; 203/8; 203/49; 203/98; 203/DIG. 7; 203/DIG. 21; 562/600
(58) Field of Search ............... 203/49, DIG. 7, 203/6, 8–9, 1, 3, 98, DIG. 21; 585/952; 562/600

(56) References Cited

U.S. PATENT DOCUMENTS

| | | | | |
|---|---|---|---|---|
| 3,674,651 A | * | 7/1972 | Otsuki et al. | 203/49 |
| 3,899,099 A | * | 8/1975 | Oiestad | 203/49 |
| 4,147,885 A | * | 4/1979 | Shimizu et al. | 562/535 |
| 4,182,658 A | * | 1/1980 | Watson | 203/69 |
| 4,260,821 A | * | 4/1981 | Benjamin | 203/49 |
| 4,780,555 A | * | 10/1988 | Bank | 556/401 |
| 5,103,032 A | * | 4/1992 | Turner et al. | 203/8 |
| 5,183,539 A | * | 2/1993 | Honma et al. | 203/38 |
| 5,969,178 A | * | 10/1999 | Okamoto et al. | 560/208 |
| 6,215,018 B1 | * | 4/2001 | Miller et al. | 560/217 |

OTHER PUBLICATIONS

Henry Z. Kister, Distillation Operation, 1990, pp. 314–315.
Takaaki Yamaguchi, Operating Manual of Chemical Apparatus, May 30, 1971, pp. 16–17 and 20–21.

* cited by examiner

Primary Examiner—Virginia Manoharan
(74) Attorney, Agent, or Firm—Mathews, Collins, Shepherd & McKay, P.A.

(57) ABSTRACT

A method for stopping a purifying column handling an easily polymerizing compound-containing solution is disclosed, which method is characterized by lowering the inner oxygen concentration of the column below the limit of oxygen concentration by supplying an inert gas to the column while the concentration of the gas of easily polymerizing compound is in the range of 100% to the lower limit of the flammable range in volume % of the purifying column or by further supplying a reflux liquid thereby cooling the interior of the column at a rate in the range of 0.01–10° C./min. This invention enjoys exceptionally high economic value in respect that it is capable of preventing the easily polymerizing compound from the occurrence of polymerization in the purifying column, precluding the interior of the purifying column from being clogged by adhesion of a polymer, and moreover avoiding the possibility of explosion.

6 Claims, 4 Drawing Sheets

METHOD FOR STOPPING PURIFYING COLUMN

BACKGROUND OF THE INVENTION

1. Field of the Invention

This invention relates to a method for stopping a purifying column which handles an easily polymerizing compound-containing solution and more particularly to a method for stopping a purifying column which, by the supply of an inert gas, lowers the oxygen concentration in the interior thereof below the limit and consequently avoids a flammable range.

2. Description of the Related Art

Such easily polymerizing compounds as acrylic acid and methacrylic acid are raw materials for commercial production and are chemical substances which are produced in a large amount at a plant of a large scale. In the case of (meth)acrylic acid, for example, the easily polymerizing compound is produced by the reaction of catalytic gas phase oxidation of propylene, isobutylene, t-butanol, methyl-t-butyl ether, or acrolein. The reaction gas obtained by this reaction of catalytic gas phase oxidation contains (meth) acrylic acid, the target product, as mixed with other by-products. For example, this reaction generates mainly non-condensable gases, namely unreacted propylene and, isobutylene, low-boiling compounds having lower boiling points than acrylic acid, namely steam and unreacted acrolein, formaldehyde produced by a side reaction, and impurities such as acetic acid, and high-boiling compounds having higher boiling points than acrylic acid, namely maleic anhydride, furfural, benzaldehyde, benzoic acid, and acrylic acid dimer. For the purpose of purifying this reaction gas thereby producing the target product, therefore, the reaction gas is washed and extracted with a counter flow water or a heavy solvent, and then the extraction is supplied to a purifying column and purifying it therein generally. Further, since the purifying column for an easily polymerizing compound is liable to give birth to a polymer of the compound owing to the properties of the compound itself, the practice of supplying a molecular oxygen-containing gas for the purpose of preventing the generation of the polymer is popularly employed.

The supply of the molecular oxygen-containing gas, however, results in enlarging the possibility of inducing explosion. When the concentration of the molecular oxygen-containing gas in the column falls within a specific range, this gas forms an explosive mixed gas and sets off explosion on exposure to a spark emitted by the static electricity. The operation of the purifying column of this nature has a high possibility of entailing combustion, explosion, and damage to equipment because the target product, solvent, generated gas, etc. are shut up in a mixed state in the purifying column. Particularly, the purifying column handling an easily polymerizing compound enlarges this possibility further because the interior of the column forms a multicomponent system and, during a start or a stop of the column, the composition in the column changes every moment unlike the operation proceeding in a stationary state.

The expression "stop of the purifying column" as used herein means an operation of stopping the supply of the raw material and the operation of accessorial devices and, at the same time, causing the interior of the purifying column to revert to the atmospheric pressure. This operation has heretofore followed more often than not the procedure of stopping the heat source and the cooling source, stopping the supply of the raw material, extracting the bottom liquid of the column, and cooling or heating the purifying column sequentially in the order mentioned, and finally causing the internal pressure of the purifying column to revert to the atmospheric pressure. There are times when the procedure of supplying a circulating liquid and a cleaning liquid in place of the raw material after the stop of the supply of the raw material to the purifying column, heating these liquids to a prescribed temperature, circulating the hot mixture of such liquids to the column thereby cleansing the interior thereof, and thereafter stopping the purifying column is performed for the purpose of expelling the residue, scale, rust, etc. from the interior of the column.

In the purifying column which particularly handles an easily polymerizing compound-containing substance, however, there are times when the easily polymerizing compound in the gaseous state condenses and induces adhesion of a polymer to the inner wall of the column, the pipes, and other accessorial devices during the course of the operation for stopping the column. Thus, the supply of the molecular oxygen-containing gas to the interior of the column is continued and the possibility of the purifying column incurring combustion and explosion persists. Particularly, the air which is supplied for allowing the inner pressure of the column to revert to the atmospheric pressure has the possibility of changing the gas composition in the column and setting off combustion and explosion on exposure to a slight impulse such as static electricity.

For the purpose of precluding such combustion and explosion, the method which comprises supplying steam to the interior of the column and causing the inner pressure of the column to revert to the atmospheric pressure has been heretofore adopted after the internal liquid of the column has been extracted from the column. In this case, the interior of the column is left cooling naturally. The natural cooling, however, requires an unduly long time till the inner temperature of the column falls to an expected level and suffers the easily polymerizing compound-containing gas to condense and form a polymer in the column. Such a polymer, in the purifying column handling such an easily polymerizing compound as (meth)acrylic acid, occurs copiously in a reboiler, a condenser, the wall of the purifying column, and in the bottom part of the column particularly after the stop of the heat source. When the polymer happens to adhere to the interior of the strainer of the extraction pump attached to the bottom of the column, however, the pump develops cavitation and ceases to operate and entails new work of removing the polymer from the interior thereof and possibly impairs the procedure for safe stop of the purifying column. Further, the adhesion of the polymer to the strainer and the consequent clogging of the strainer necessitate a cleansing operation. The chemical irritations from the raw material for reaction, the reaction product, and the by-products and the physical hindrances due to the adhesion of the polymer inflict spiritual displeasure on workers and bring an alarming influence on the workers' health. Further, the organic solvent used for distillation has the problem of jeopardizing the safety of the operation of the column by ignition. It is generally difficult to remove and discard the adhering polymer with human power, because of the huge purifying column and devices to be cleaned.

The work of cleansing the purifying column and other devices attached thereto for the removal of the polymerizing substance generated therein or adhered thereto necessitates a large volume of a detergent solvent. When the used detergent is discarded or disposed of as by combustion, however, the treatment entails generation of carbon dioxide and inevitable release of the organic solvent into rivers and coasts, it causes the result that the spirit of environmental protection will be spoiled. Moreover, the waste liquid resulting from the use of the detergent also requires a treatment for disposal, which forms the matter for improvement in the viewpoint of not merely economy but also environmental preservation.

Further, when a polymerization inhibitor is used for the purpose of precluding polymerization and clogging due to the easily polymerizing compound, the polymerization inhibitor has a high boiling point and, therefore, is incapable of preventing the easily polymerizing substance left in the gas from yielding to polymerization. If it is used actually at all, it will fail to produce a sufficient effect of preventing the polymerization because the easily polymerizing compound is liable to condense and induce polymerization.

When water is intentionally introduced into the column to induce swift cooling of the interior of the column for the purpose of preventing the generation of a polymer due to the effect of heat on the easily polymerizing compound, the used cooling water persists in the column and renders the recovery of the inner liquid of the column usable as a raw material compound difficult. This situation necessitates a special treatment for discarding the inner liquid of the column which is no longer usable.

SUMMARY OF THE INVENTION

The present inventor, as the result of a deliberate study of the ratio of the gas of an easily polymerizing compound and the oxygen gas produced in the conventional method for stopping the purifying column, has found that the conventional method suffers in that the easily polymerizing substance persists in a gaseous form in the purifying column even after the supply of raw material liquid is stopped and the bottom liquid of the column is extracted and, when air is introduced into the column in such condition and enabled to effect reversion of the inner pressure of the column to the atmospheric pressure, suffers in that the ratio of the easily polymerizing compound and the oxygen gas in the column vary in the direction of enlarging the possibility of combustion and explosion. He has further found that the purifying column can be stopped without going through the flammable range of the column without reference to the degree of concentration under the inner pressure of the column below a specific volume % and that the purifying column can be swiftly cooled and consequently the easily polymerizing compound in the column can be prevented from succumbing to polymerization by stopping the purifying column while supplying a reflux liquid to the condenser attached to the purifying column. This invention has been perfected as a result.

To be specific, the task implied above is accomplished by the following invention.

This invention concerns a method for stopping a purifying column handling an easily polymerizing compound-containing solution, characterized by lowering the inner oxygen concentration of the column below the limit of oxygen concentration by supplying an inert gas to the column while the concentration of the gas of easily polymerizing compound is in the range of 100% to the lower limit of the flammable range in volume % of the purifying column.

As a method for stopping a purifying column containing an easily polymerizing compound, by supplying an inert gas while the concentration of the gas of easily polymerizing compound is in the range of 100% to the lower limit of the flammable range in volume % of the purifying column and thereby adjusting the inner oxygen concentration of the column below the limit of oxygen concentration, it is made possible to preclude the easily polymerizing compound from explosion and combustion and, at the same time, promptly cool the inner temperature of the column and prevent the otherwise possible polymerization. Further, by cooling the inner column by the use of a feed liquid, it is made possible to avoid explosion and combustion and prevent the polymerization. This invention enjoys exceptionally high economic value as a method for stably stopping the purifying column while infallibly avoiding explosion and combustion and preventing polymerization.

DETAILED DESCRIPTION OF THE PREFERRED EMBODIMENTS

This invention primarily concerns a method for stopping a purifying column handling an easily polymerizing compound-containing solution, characterized by lowering the inner oxygen concentration of the column below the limit of oxygen concentration by supplying an inert gas to the column while the concentration of the gas of easily polymerizing compound is in the range of 100% to the lower limit of the flammable range in volume % of the purifying column. It has been ascertained by pursuing an elaborate study of the flammable range in a purifying column that the flammable range can be avoided and consequently the purifying column can be stopped safely by adjusting the inner oxygen concentration of the column below the limit of oxygen concentration at a certain step in the operation of stopping the purifying column. Now, this invention will be described in detail below.

The purifying column forms a multi component system containing the solvent, the target product, the by-products, etc. The flammable range of this system is fixed by composition of the oxygen concentration and a combustible gas concentration. Actually, when the easily polymerizing compound happens to be acrylic acid, the flammable range is fixed by the volume ratio of the oxygen concentration and the concentration of acrylic acid gas in the column. This invention, by lowering the oxygen concentration below the limit thereof, is enabled to avoid the flammable range due to the inner gas composition of the column even when the inner gas composition of the purifying column is varied by the operation of stopping the purifying column handling the easily polymerizing compound solution. This situation will be described with reference to FIG. 2 and FIG. 1 by adducing the case of stopping the operation of an acrylic acid purifying column as one example.

Figure 2:
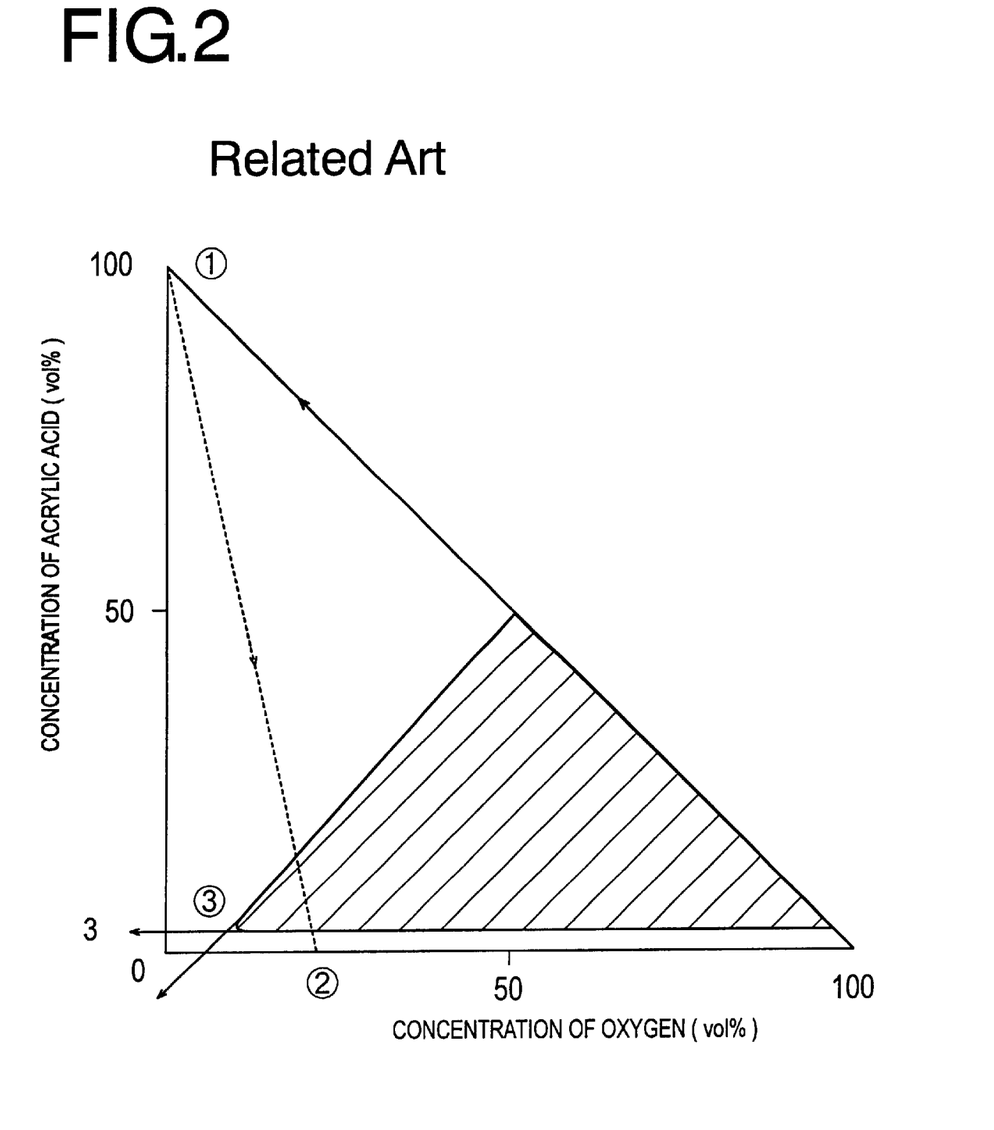
FIG. 2 is a diagram illustrating the flammable range in the relation between concentration of acrylic acid gas and oxygen gas in a purifying column for acrylic acid during the stop of the purifying column according to the conventional method; the area shaded with oblique lines representing a flammable range.

FIG. 2 shows the ratio of the gases of acrylic acid and oxygen at the top of the purifying column. In the diagram of FIG. 2, the horizontal axis is the scale of the concentration of oxygen and the vertical axis the scale of the concentration of acrylic acid and the part shaded with oblique lines represents the flammable range. The expression "the lower limit of the flammable range of an easily polymerizing compound gas, by vol. %" as used herein means the lowest magnitude of the concentration of the easily polymerizing compound in the gas composition forming the flammable range. The term "the limit of oxygen concentration" means the lowest value of the concentration of oxygen in the gas composition forming the flammable range. The point of intersection between these two limits in the acrylic acid purifying column is indicated by the mark, ③. During the distillation of acrylic acid, the concentration of acrylic acid gas is about 100 vol. % and that of oxygen at 0 vol. % at the top of the column. The gas composition in the column top part falls at the position of ①. When the purifying tower in the condition is stopped and then opened to induce reversion of the inner pressure of the column to the atmospheric pressure, the concentration of acrylic acid gas becomes 0 vol. % and the concentration of air similarly to that of air becomes 21 vol. % in the purifying column, namely they reach the position of ②. To be specific, even when such operations as stopping the supply of the raw material and stopping the heat source are performed from the state of ①, the concentration of the acrylic acid gas in the column is merely lowered from 100 vol. % and the concentration of oxygen is merely increased by the introduction of air. When the air having an oxygen concentration of 21 vol. % is introduced for the purpose of causing the inner pressure of the column to revert to the atmospheric pressure, the position of ② representing the concentration of acrylic acid gas of 0 vol. % and the concentration of oxygen of 21 vol. % is eventually reached along the dotted line from the position of shown in FIG. 2. Particularly in the purifying column handling an easily polymerizing compound-containing solution, more often than not such molecular oxygen-containing gas as air is supplied to the purifying column for the purpose of preventing polymerization. After the operation of the purifying column is stopped, it becomes necessary to supply the gas for enabling the inner pressure of the column to revert to the atmospheric pressure. When the supply of the air is continued after the supply of the raw material and the heat source are stopped, the interior of the column never fails to pass the flammable range. This invention has established by the discovery that the flammable range fixed by the easily polymerizing compound gas and the oxygen gas exists on the straight line interconnecting the points ① and ② and that the passage through the flammable range is enabled to be avoided without reference to the concentration of the gas of acrylic acid by introducing the inert gas and lowering the concentration of oxygen below the limit thereof, preferably not higher than 9 vol. % while this concentration of gas of acrylic acid is in a specific range. In FIG. 2, the limit of oxygen concentration is shown to be 9.5 vol. %.

Figure 1:
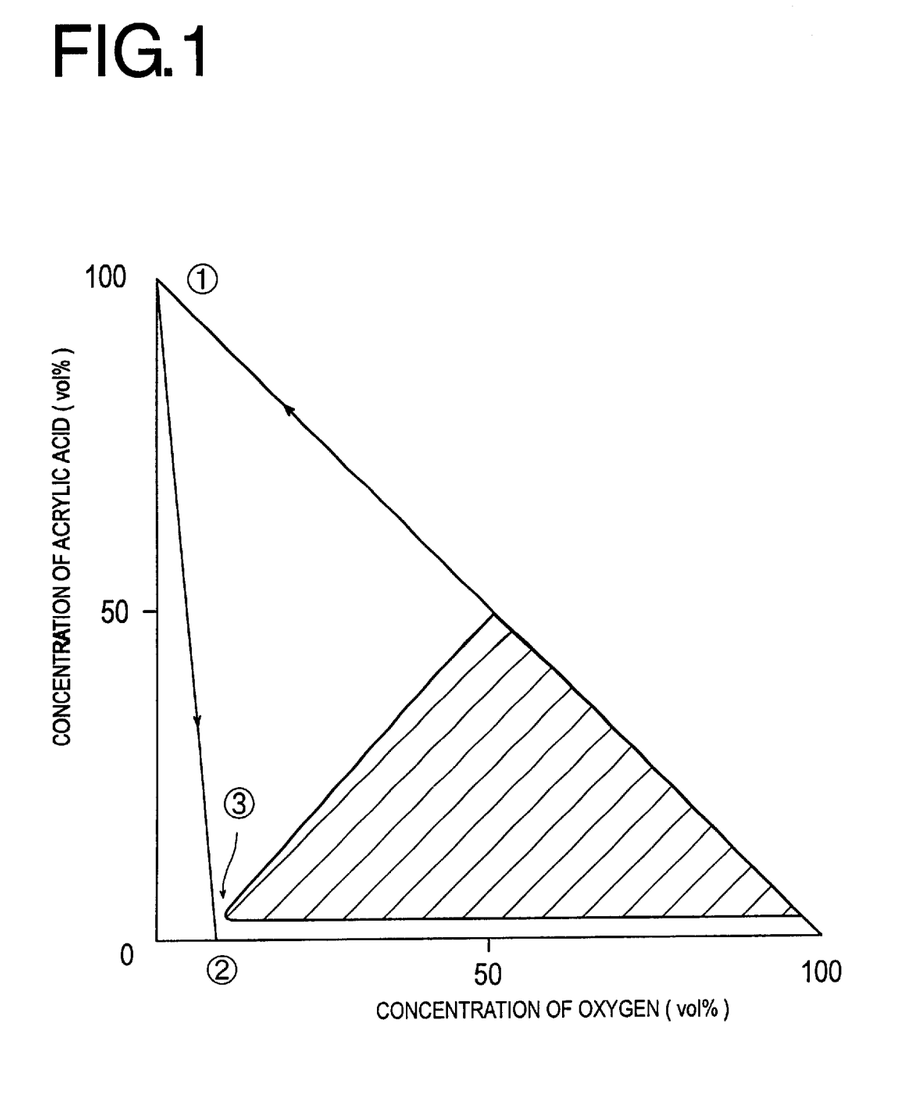
FIG. 1 is a diagram illustrating the flammable range in the relation between acrylic acid gas and oxygen gas in a purifying column for acrylic acid during the stop of the purifying column according to this invention; the area shaded with oblique lines representing a flammable range.

Now, the ratio of the gases of acrylic acid and oxygen obtained by the method for stopping the purifying column according to this invention will be described below with the aid of FIG. 1. In the diagram of FIG. 1, the mark ① represents the ratio of the gases of acrylic acid and oxygen while the operation of the purifying column is in the stationary state and, similarly to the diagram of FIG. 2, the concentration of acrylic acid gas falls at the position of 100 vol. % and that of oxygen at the position of 0 vol. %. The area shaded with oblique lines in FIG. 1 is the flammable range similarly to FIG. 2. The point of intersection of "the lower limit of the flammable range of the easily polymerizing compound gas, vol. %" and "the limit of the oxygen concentration" is indicated with the mark ③. When the supply of the inert gas is initiated from the state of ① during the operation of the purifying column, the concentration of oxygen gas can be lowered below the limit of oxygen concentration while the inner concentration of the acrylic acid gas of the purifying column is in the range from 100 vol. % to the lower limit of the flammable range of the easily polymerizing compound gas shown by the mark ③ because the concentration of acrylic acid does not increase with the elapse of time unless acrylic acid is supplied anew. This invention has clarified the flammable range to be formed by the ratio of the gases of an easily polymerizing compound and oxygen during the stop of the purifying column. Thus, by clarifying the limit of oxygen concentration at the mark ③ in the diagram of FIG. 1 to be 9.5 vol. % and lowering the oxygen concentration in the range from the mark ① to the mark ③ representing "the lower limit of the flammable range of the easily polymerizing compound gas in vol. %" below the limit of oxygen concentration, preferably not higher than 9 vol. % by supplying a inert gas, the avoidance of the flammable range can be easily attained even during the operation of stopping the purifying column which incurs variation of gas composition. The flammable range during the operation of stopping the purifying column has never been clarified and therefore the steam has been introduced into the purifying column in order to precluding the combustion. This invention enables the operation of the purifying column to be easily and safely stopped by based on a development of such flammable range. The flammable range can be found by using an explosion limit measuring device developed by the U.S. Bureau of Mining or an explosion limit measuring device developed by Kitagawa Research Institute.

Incidentally, at the position of ② at which the oxygen concentration is 9 vol. % while the concentration of acrylic acid gas is 0 vol. %, the oxygen concentration is below the limit thereof when the purifying column is stopped by the method contemplated by this invention. Since this invention contemplates lowering the oxygen concentration in the purifying column below the limit of oxygen concentration, preferably not higher than 9 vol. % in the range of the lower limit of the flammable range of the easily polymerizing compound gas" with a view to avoiding the passage through the flammable range, the act of opening the purifying column and introducing the air till the oxygen concentration reaches 21 vol. % after effecting passage through the position of ② representing the oxygen concentration of not higher than 9 vol. % at the concentration of acrylic acid gas at 0 vol. %, for example is embraced in the embodiment of this invention.

The "purifying column" to which this invention is directed embraces all types of purifying columns which handle an easily polymerizing compound-containing solution, no matter whether they have the designation of "purifying column." The purifying columns which have been heretofore called as dehydrating column, low boiling separating column, high boiling separating column, and azeotropic separating column, therefore, are invariably subjected to the treatment by the method of this invention so long as the solutions supplied to these columns for the purpose of the treatment mentioned above are solutions containing easily polymerizing compounds. The "easily polymerizing compound-containing solution" is only required to contain an easily polymerizing compound. The concentration of this compound in the solution and the choice of the solvent used for the solution between an organic solvent and an aqueous solvent do not matter.

As concrete examples of the "easily polymerizing compound," such carboxylic acids as acrylic acid, methacrylic acid, fumaric acid, and maleic acid which possess an unsaturated double bond and esters thereof may be cited. The hydroxyl group-containing compound for forming the ester with a carboxylic acid possessing such an unsaturated double bond as mentioned above is preferred to be a lower aliphatic alcohol or a lower alicyclic alcohol each of 1–12 carbon atoms. As concrete examples of the hydroxyl group-containing compound, various alcohols such as methanol, ethanol, propanol, isopropanol, n-butanol, isobutanol, sec-butanol, t-butanol, 1-pentanol, 2-phetanol, 3-pentanol, cyclopentanol, 1-hexanol, 2-hexanol, 3-hexanol, cyclohexanol, 1-heptanol, 2-heptanol, 3-heptanol, 1-octanol, isooctanol, 2-ethylhexanol, isononyl alcohol, and lauryl alcohol may be cited. These alcohols may be in a linear state or a branched state. These alcohols may be used either singly or in the form of a combination of two or more members.

As concrete examples of the solvent for containing such an easily polymerizing compound as mentioned above, not only water and an organic acid-containing water but also the middle extracted fraction produced in the distillation of paraffin, diphenyl ether, diphenyl, the mixture of the liquids mentioned above such as, for example, the mixture of 70–75 wt % of diphenyl ether and 25–30 wt % of diphenyl, and the mixture formed by blending the mixture of 70–75 wt % of diphenyl ether and 25–30 wt % of diphenyl with 0.1–25 wt % of o-diphenyl phthalate may be cited.

As a method for separating the solvent containing the easily polymerizing compound, water and the low boiling impurity, the distillation by the use of an azeotropic solvent is in common use. Specifically, this separation is effected by expelling the azeotropic solvent and water by evaporation through the top of an azeotropic separating column and recovering acrylic acid through the bottom of the column. As a concrete examples of the azeotropic solvent, at least one kind of solvent selected from the group consisting of heptane, dimethyl cyclohexane, ethyl cyclohexane, toluene, ethyl benzene, chlorobenzene, xylene, and mixtures thereof;

at least one kind of solvent selected from the group consisting of diethyl ketone, diisopropyl ketone, methylpropyl ketone, methylisobutyl ketone, methyl-t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valerate, ethyl acetate, methyl acrylate, dibutyl ether, and mixtures thereof; and the mixed solvent of at least one kind of solvent selected from the group consisting of heptane, dimethyl cyclohexane, ethyl cyclohexane, toluene, ethyl benzene, chlorobenzene, xylene, and mixtures thereof and at least one kind of solvent selected from the group consisting of diethyl ketone, diisopropyl ketone, methylpropyl ketone, methylisobutyl ketone, methyl-t-butyl ketone, n-propyl acetate, n-butyl acetate, ethyl acrylate, methyl methacrylate, ethyl methacrylate, vinyl acrylate, n-propyl acrylate, allyl acetate, isopropenyl acetate, vinyl propionate, propyl propionate, methyl crotonate, methyl valerate, ethyl acetate, methyl acrylate, dibutyl ether, and mixtures thereof may be cited.

The inert gases of the kind contemplated by this invention include nitrogen gas, carbon dioxide, gases having oxygen concentrations of not higher than the limit of oxygen concentration of flammable range, and mixtures thereof, for example. This invention prefers the inert gas to be a gas having an oxygen concentration of not higher than 9 vol. % or nitrogen gas. Then, it is allowable for the purpose of lowering the oxygen concentration in the column below the limit of oxygen concentration to supply nitrogen gas as an inert gas in the amount of up to at least 20 vol. % of the total inner volume of the column and then supply air. By the supply of such different inert gases as mentioned above, the concentration of oxygen can be lowered below the limit of oxygen concentration without using expensive nitrogen gas.

Now, the mode of embodying the method of this invention for stopping the acrylic acid purifying column will be described below with the aid of FIG. 3.

Figure 3:
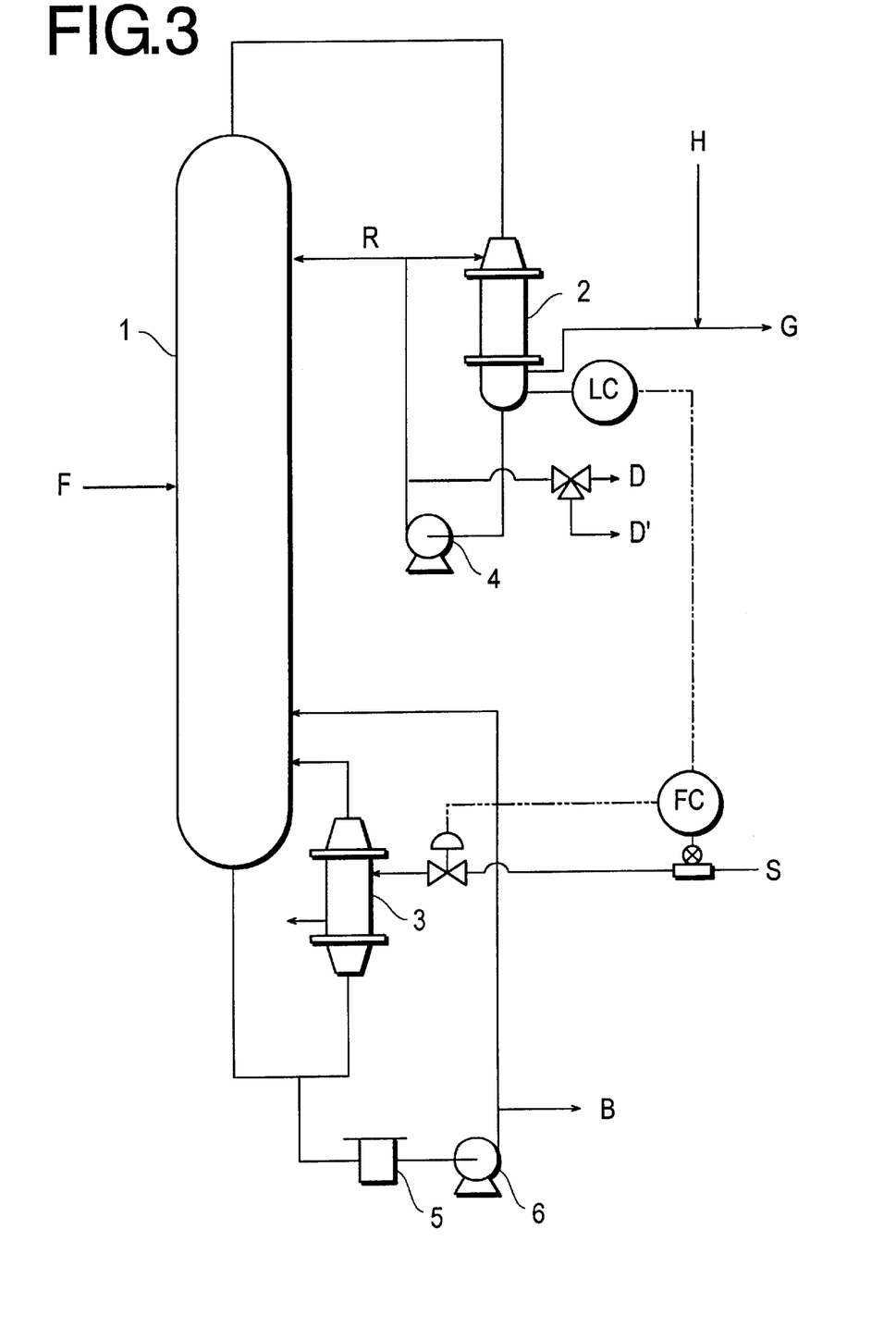
FIG. 3 is a diagram schematically illustrating a purifying column for implementing the method for stopping according to this invention.

As used in the diagram of FIG. 3, 1 denotes a purifying column, 2 a condenser, 3 a reboiler, 4 and 6 each a pump, 5 a strainer, F a feed orifice for the raw material, R a reflux liquid, D a discharge liquid, B a bottom liquid of the column, G an uncondensated gas, H a supply orifice of the inert gas and S steam.

The raw material liquid to be supplied to the purifying column is the bottom liquid of a low boiling separating column which is formed by absorbing an acrylic acid-containing gas obtained by the reaction of catalytic gas phase oxidation of propylene, propane, or acrolein in an absorbing solution and subjecting this solution to a distilling treatment in order to expelling, water and low boiling compounds having low boiling point from acrylic acid by evaporation from the solution. The purifying column (1) is a high boiling separating column in the view of introduce the bottom liquid of a low boiling separating column thereto and then removing a high boiling compound contained in the bottom liquid.

To begin with, the composition of the acrylic acid-containing solution to be supplied to the purifying column cannot be generally specified because it is variable under the conditions of the component steps of the process. The solution, for example, may comprise 90–99 wt % of acrylic acid, 1–1000 wt ppm of acetic acid, 1–1000 wt ppm of water, and 1–10 wt % of acrolein, formaldehyde, maleic anhydride, furfural, benzaldehyde, or acrylic acid dimer. The column top pressure during the operation of the column is generally under a reduced pressure, preferably a pressure in the range of from the absolute pressure 10–150 hPa. The feed material is supplied through the feed orifice F to a high boiling separating column which is a purifying column (1). In this column, the bottom liquid of the column is heated by the supply of the steam S or by means of the reboiler (3) so that part of the bottom liquid of the column is passed through the strainer (5) and removed solid matter and circulated to the bottom part of the purifying column (1). After the acrylic acid as the target product has been evaporated through the top of the purifying column (1) and condensed by the condenser (1), the product is recovered as D. Part of the reflux liquid is circulated by the pump 4 to the purifying column (1). Incidentally, a part of the bottom liquid of the column is recovered as B and the polymerization inhibitor is delivered to the condenser (2) to dissolve in the reflux liquid and supply to the purifying column (1). For the purpose of preventing the polymerization, the reboiler (3) is supplied with air as a molecular oxygen-containing gas (not shown).

The purifying column is stopped by the following method.

(i) For a start, the distillate at the top of the purifying column (1) is discharged by changing the line D into D' (the line for recovering a rejected product). At this time, the concentration of the gas of acrylic acid in the top of the column is in the range of 90–100 vol. % and the concentration of oxygen in the range of 0–5 vol. %.

(ii) Then, the supply of the raw material F through the feed orifice is stopped. Though the stop of the supply of the raw material means a stop to the supply of fresh acrylic acid, the concentration of the gas of acrylic acid is brought to a level in the range of 88.0–99.9 vol. % and the concentration of oxygen to a level in the range of 0.1–7.0 vol. % respectively in the top of the column in consequence of the continued supply of the molecular oxygen-containing gas into the purifying column (1).

(iii) The supply of steams to the reboiler (3) is stopped.

(iv) The supply of the reflux liquid to the column (1) is stopped. The concentration of the gas of acrylic acid is brought to a level in the range of 88.0–99.9 vol. % and the concentration of oxygen to a level in the range of 0.1–7.5 vol. % respectively in the top of the column inconsequence of the continued supply of the molecular oxygen-containing gas. Optionally, the step (iv) and the step (iii) may be simultaneously carried out.

(v) The supply of the molecular oxygen-containing gas is stopped. The concentration of the gas of acrylic acid is in the range of 88.0–99.9 vol. % and the concentration of oxygen in the range of 0.1–7.5 vol. % respectively in the top of the column. Optionally, the step (v) may be carried out simultaneously with the step (iii) or the step (iv).

(vi) The extraction of the bottom liquid of the column B through the line for the bottom liquid of column is stopped.

(vii) The supply of the polymerization inhibitor is stopped.

(viii) The supply of the liquid to the condenser (2) is stopped. The liquid condensed in the condenser (2) is partly returned as the reflux liquid to the column (1) and partly recovered as the distillate through the line for the discharge liquid D. For the prevention of the polymerization in the condenser (2), the liquid is constantly circulated from the upper part of the condenser (2) by means of the pump (4). The foregoing expression "the stop of the supply of the liquid to the condenser (2)" refers to the stop of the circulation of the liquid to the condenser (2).

Figure 4:
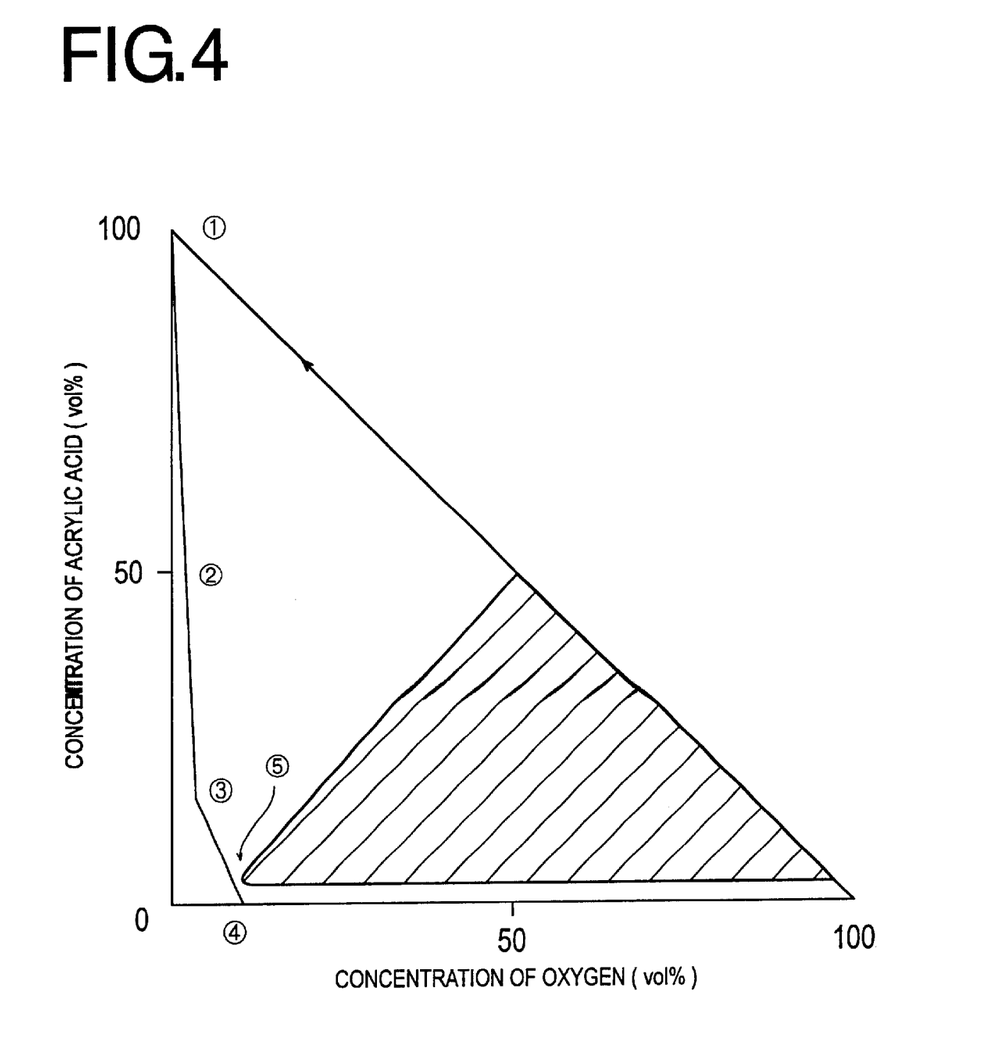
FIG. 4 is a diagram illustrating the flammable range in the relation between concentration of acrylic acid gas and oxygen gas in a purifying column for acrylic acid during the stop of the purifying column according to this invention's method in the case of supplying air after nitrogen gas has been supplied as an inert gas; the area shaded with oblique lines representing a flammable range.

(ix) Next, the supply of the inert gas through the top of the purifying column (1) is started. When the operation of the purifying column (1) is being carried out in a vacuum system, for example, it is commendable to heighten the pressure to a level in the range of 500–1000 hPa by supplying nitrogen gas as an inert gas and then effect reversion of the pressure to the atmospheric pressure by the supply of air. Once the concentration of the acrylic acid gas in the column has been made to reach a level in the range of 0.1–40 vol. % by the increase of the pressure with nitrogen gas, the oxygen concentration at the time the concentration of acrylic acid gas is 3 vol. % will not exceed the limit of oxygen concentration and, as a result, the flammable range will be avoided even when air is supplied thereafter. Moreover, by using nitrogen gas and air, it is made possible to decrease the amount of expensive nitrogen gas to be used. The method for avoiding the flammable range due to arrangement of the gases ratio between acrylic acid and oxygen in the operation using the nitrogen gas and oxygen is illustrated in FIG. 4. In the diagram of FIG. 4, the mark ① represents the composition of the acrylic acid gas in the top of the purifying column during the normal operation. The ratio of gases of acrylic acid and oxygen in the condition assumed after the steps of (i)–(viii) is shown by the mark ②. When nitrogen gas is then supplied to the interior of the column, the ratio reaches the position of ③. At this time, the inner pressure of the column is 700 hPa. Then, air is supplied till the inner pressure of the column finally reverts to the atmospheric pressure. This position is shown by the mark ④. Incidentally, the lower limit of the flammable range of the acrylic acid gas in the purifying column is 3 vol. % and the point of intersection with the limit of oxygen concentration is shown by the mark ⑤. In FIG. 4, the limit of oxygen concentration is found to be 9.5 vol. %. By the operation of this step of (ix), the interior of the column is simultaneously cooled at a rate in the range of 0.01–1.0° C./min. Incidentally, the final inner temperature of the column reached by the cooling is in the range of from 15° C. to the temperature of 20° C. higher than the ambient temperature.

(x) The inner liquid of the column is extracted and the operation of stopping the purifying column is terminated.

In the purifying column which handles an easily polymerizing compound-containing solution, the supply of oxygen gas is effective in preventing the easily polymerizing compound from polymerization. The method which accomplishes the avoidance of the flammable range by heightening the oxygen concentration once and subsequently lowering the oxygen concentration by the supply of some other gas encounters difficulty in attaining the adjustment of the concentration of acrylic acid gas and the concentration of oxygen. This invention, therefore, is characterized by lowering the inner oxygen concentration of the column below the limit of oxygen concentration by the supply of an inert gas while, during the operation of stopping the purifying column, the concentration of the easily polymerizing compound gas is in the range of 100% of the purifying column to the lower limit of the flammable range. Incidentally, as illustrated in FIG. 4 and described above, the concentration of acrylic acid gas is 3 vol. % when the limit of oxygen concentration in the flammable range is 9.5 vol. %. When the concentration of acrylic acid gas is not higher than 3 vol. %, therefore, the oxygen concentration does not need to be limited below 9.5 vol. %.

As the way of supplying the inert gas, the conventional method which consists in supplying a molecular oxygen-containing gas or the method which resides in supplying an inert gas through a vacuum line at the top of the column may be adopted, for example. To be specific, the inert gas may be directly mixed with the bottom liquid of the column by means of bubbling or the inert gas may be dissolved in a solvent and indirectly mixed with the bottom liquid. The bubbling can be easily accomplished by supplying from the bottom of the purifying column and/or the reboiler a gas having an oxygen concentration below the limit of oxygen concentration, preferably not higher than 9 vol. %. Particularly, the supply which is made through the medium of the reboiler proves particularly advantageous because it can particularly effectively prevent the polymerization also inside the reboiler.

This invention, when embodied in the method for stopping the purifying column, is preferred simultaneously to cool the interior of the column at a rate in the range of 0.01–10° C./min. In the conventional operation of stopping the purifying column, the stop of the supply of the raw material or the supply of steam to the reboiler immediately results in stopping the supply of the reflux liquid from the condenser, the easily polymerizing compound condenses on the inner wall of the column and induces adhesion of a polymer to the wall because the easily polymerizing compound remains in a gasified state inside the purifying column even after the stop of the supply of the raw material. It has been found that when the interior of the purifying column is swiftly cooled at a rate in the range of 0.01–10° C./min. during the operation of stopping the purifying column with a view to solving the trouble, the polymerization can be prevented because the easily polymerizing compound in the gaseous state is quickly liquefied and recovered in the bottom liquid of the column. The cooling in this case may be effected by supplying an inert gas into the interior of the column or by supplying a reflux liquid. It is particularly advantageous to supply the reflux liquid from the top of the purifying column or from the intermediate stage of the column. The polymerization due to the condensation of the easily polymerizing compound in the gaseous state can be prevented by the circulation of the reflux liquid in the manner described above because the inner wall of the column is covered with the reflux liquid and the gas of easily polymerizing compound is easily dissolved in the cooled reflux liquid on contact therewith. The interior of the column can be cooled also by supplying the reflux liquid into the interior of the condenser.

As the reflux liquid under discussion, the solvent which is used for the easily polymerizing compound-containing solution can be used in its unmodified form. The bottom liquid of the column may be likewise used as the reflux liquid. Incidentally, the reflux liquid may be supplied from the top of the column or from the intermediate stage of the column through the medium of a delivery line which is additionally disposed. It may be otherwise supplied through the medium of a condenser attached to the purifying column. When the condenser serves as the medium, the reflux liquid comes to be supplied into the column from the place to which the reflux liquid from the condenser is circulated.

In this invention, the reflux liquid supplied to the interior of the column may contain a polymerization inhibitor. The polymerization inhibitor so contained in the reflux liquid is effective in preventing the easily polymerizing compound from polymerization.

As concrete examples of the polymerization inhibitor which is advantageously used herein, at least one member selected from the group consisting of hydroquinone, methoxyhydroquinone, hydroquinone monomethyl ether, cresol, phenol, t-butyl catechor, diphenyl amine, phenothiazine, and methylene blue, at least one member selected from the group consisting of such copper salt compounds as copper dimethyldithiocarbamate, copper diethyldithiocarbamate, copper dibutyldithiocarbamate, and copper salicylate, and such manganese salt compounds as manganese acetate, and p-phenylene diamines such as p-phenylene diamine, N-oxyl compounds such as 4-hydroxy-2,2,6,6-tetramethylpiperidinoxyl, ureas such as urea, and thioureas such as thiourea may be cited. The compounds enumerated above may be used either singly or on the form of a combination of two or more members.

The polymerization inhibitor is supplied to the purifying column (1) in the stationary state so that the concentration of the polymerization inhibitor in the bottom of the column is generally in the range of 0.01–50 wt %, preferably in the range of 0.01–30 wt %, and particularly preferably in the range of 0.01–23 wt %. When water and a low boiling substance are removed from the acrylic acid-containing solution, for example, the distillation is performed under normal pressure or under a reduced pressure, preferably under an operating pressure in the range of the absolute pressure 100–1013 hPa, at the bottom temperature of the column in the range of 60–120° C. The concentration of the polymerization inhibitor in the bottom liquid of the column is generally in the range of 0.01–1.0 wt %. When the high boiling substance is removed from the acrylic acid-containing solution, the distillation is carried out under a reduced pressure, preferably under an operating pressure in the range of the absolute pressure 10–150 hPa, at the bottom temperature of the column in the range of 60–120° C. The concentration of the polymerization inhibitor in the bottom liquid of the column is generally in the range of 0.01–15 wt %.

Now, the method for stopping the purifying column by cooling the interior of the column at a rate in the range of 0.01–10° C./min will be described further below with the aid of FIG. 3. The symbols used in FIG. 3 and the composition of the liquid supplied to the purifying column, and the conditions of distillation involved herein are the same as those used in the description of the method for stopping the purifying column by the supply of an inert gas illustrated in FIG. 3. Further, the operation for stopping the purifying column in the steps (i)–(iii) is identical with the method for stopping the purifying column by supplying the inert gas mentioned above thereby lowering the concentration of oxygen gas below the limit of oxygen concentration as described above.

To be specific, (i) the distillate at the top of purifying column (1) is discharged by changing the line D into D' (the line for recovering a rejected product). At this time, the concentration of the acrylic acid gas is in the range of 90–100 vol. % and the concentration of oxygen in the range of 0–5 vol. %.

(ii) Subsequently, the supply of the raw material F through the feed orifice is stopped. The stop of the supply of the raw material results in stopping the supply of fresh acrylic acid. The concentration of acrylic acid gas is brought to a level in the range of 88.0–99.9 vol. % and the concentration of oxygen in the range of 0.1–7.0 vol. % in consequence of the continued supply of the oxygen gas into the purifying column (1).

(iii) The supply of steams to the reboiler (3) is stopped.

(iv) When the inner temperature of the column begins to fall, the supply of the molecular oxygen-containing gas to the reboiler (3) is stopped. The concentration of acrylic acid gas reaches a level in the range of 86.5–99.9 vol. % and the concentration of oxygen in the range of 0.1–8.5 vol. % in consequence of the stop of the supply of a fresh gas to the interior of the purifying column (1).

(v) The inner temperature of the column is lowered by the continuous circulating supply of the reflux liquid from the condenser (2) till it reaches a level in the range of from the temperature of 15° C. to the temperature of 30° C. higher than the ambient temperature. Then, the amount of the reflux liquid is gradually decreased till the supply is finally stopped. The inner temperature of the column is cooled at a rate in the range of 0.5–10°

C./min. In consequence of the stop of evaporation from the top of the column, the concentration of acrylic acid gas in the top of the column reaches a level in the range of 86.0–99.9 vol. % and the concentration of oxygen in the range of 0.1–9 vol. %. Incidentally, the cooling of the column with the reflux liquid is accomplished by supplying the aforementioned acrylic acid-containing solution having contained a polymerization inhibitor therein to the condenser (2) attached to the purifying column (1), cooling this solution to a level in the range of from 15° C. to the temperature of 20° C. not higher than the ambient temperature, and circulating the cooled solution. In this case, the amount of the reflux liquid is preferred to be enough for wetting wholly the inner surface of the condenser. Thus, the polymerization which occurs during the condensation of the gas of easily polymerizing compound can be prevented even when the gas is supplied into the condenser.

(vi) The extraction of the bottom liquid B of the column from the bottom is stopped.

(vii) The supply of the polymerization inhibitor is continued and (viii) the supply of the liquid to the condenser (2) is also continued.

(ix) To the purifying column (1), an inert gas having a temperature in the range of from 0° C. to the temperature of 20° C. not higher than the ambient temperature is supplied. In consequence of the stop of the supply of fresh gas into the interior of the purifying column (1), the concentration of oxygen at the time the concentration of acrylic acid gas is 3 vol. % is not higher than the limit of oxygen concentration and in the range of 0.1–9 vol. %. At this time, the inner temperature of the column is cooled at a rate in the range of 0.01–1.0° C/min. Unlike the procedure described above, the cooling of the interior of the column by the supply of the inert gas at the step (ix)' may be performed after the supply of the polymerization inhibitor is stopped at the step (vii)' and the supply of the liquid to the condenser (2) is stopped at the step of (viii)'. The interior of the column may be cooled solely with the inert gas. Subsequently, (x)' the extraction of the liquid from the interior of the column is carried out and the operation of stopping the purifying column is terminated.

The embodiment of this invention does not need to be limited to the method described above but may be applied otherwise. Subsequently to the steps (i)–(iii) mentioned above, the following procedure is adopted for the remainder of the process led by the step (iv).

(iv)' The circulating supply of the reflux liquid from the condenser (2) into the column is stopped. In consequence of the continuation of the supply of the molecular oxygen-containing gas, the concentration of acrylic acid gas reaches a level in the range of 87.5–99.9 vol. % and the concentration of oxygen in the range of 0.1–7.5 vol. % in the top part of the column. The step (iv)' may be carried out simultaneously with the step (iii).

(v)' The supply of the molecular oxygen-containing gas is stopped. The concentration of acrylic acid gas is in the range of 87.5–99.9 vol. % and the concentration of oxygen in the range of 0.1–7.5 vol. %. Incidentally, the step (v)' may be carried out simultaneously with the step (iii) or the step (iv)'.

(vi)' The extraction of the bottom liquid B of the column from the bottom is stopped.

(vii)' The supply of the polymerization inhibitor is continued and (viii)' the supply of the liquid to the condenser (2) is also continued. The inner temperature of the column in this case is cooled at a rate in the range of 0.5–10° C./min.

(ix)' To the purifying column (1), an inert gas having a temperature in the range of from 0° C. to the temperature of 20° C. not higher than the ambient temperature is supplied. In consequence of the start of the supply of a fresh gas to the interior of the purifying column (1), the concentration of oxygen is not higher than the limit of oxygen concentration and in the range of 0.1–9 vol. % at the time the concentration of acrylic acid gas is 3 vol. %. At this time, the inner temperature of the column is cooled at a rate in the range of 0.01–1.0° C./min. Unlike the procedure described above, the cooling of the interior of the column by the supply of the inert gas at the step (ix)' may be carried out after the supply of the polymerization inhibitor is stopped at the step (vii)' and the supply of the liquid to the condenser (2) is stopped at the step (viii)'. The interior of the column can be cooled solely with the insert gas. Then, (x)' the inner liquid of the column is extracted and the operation of stopping the purifying column is terminated.

The embodiment of this invention may be applied otherwise. Subsequently to the steps (i)–(iii) mentioned above, for example, the following procedure is adopted for the remainder of the process led by the step (iv).

(iv)" The supply of the molecular oxygen-containing gas to the reboiler (3) is stopped when the inner temperature of the column begins to fall. In consequence of the start of the supply of fresh gas into the purifying column (1), the concentration of acrylic acid gas reaches a level in the range of 86.5–99.9 vol. % and the concentration of oxygen in the range of 0.1–8.5 vol. % at the time the supply of the gas is stopped.

(v)" When the inner temperature of the column is lowered by the continued supply of the reflux liquid into the column and the inner temperature of the column reaches a level in the range of from 15° C. to the temperature of 30° C. higher than the ambient temperature. The inner temperature of the column is cooled at a rate in the range of 0.5–10° C./min. In consequence of the stop of the evaporation from the top of the column, the concentration of acrylic acid gas reaches a level in the range of 86.0–99.9 vol. % and the concentration of oxygen in the range of 0.1–9 vol. %.

(vi)" The extraction of the bottom liquid B of the column from the bottom is stopped.

(vii)" The supply of the polymerization inhibitor is stopped.

(viii)" The supply of the liquid to the condenser (2) is stopped.

(ix)" The inert gas is supplied to the purifying column (1) through the top thereof. By this operation, the interior of the column is simultaneously cooled at a rate in the range of 0.01–1.0° C. The inner temperature of the column is cooled till it finally reaches a level in the range from 15° C. to the temperature of 20° C. not higher than the ambient temperature. At this time, the concentration of oxygen is not higher than the maximum of oxygen concentration and in the range of 0.1–9 vol. % at the time the concentration of acrylic acid gas in the top of the column is 3 vol. %.

(x)" The inner liquid of the column is extracted and the operation of stopping the purifying column is terminated.

The description given above has concerned the method for stopping the purifying column for an acrylic acid-containing solution. By changing the composition of the raw material liquid supplied to the purifying column to methacrylic acid, this invention is enabled to be applied to the purifying column used for distilling a methacrylic acid-containing solution.

This invention can be likewise applied to the purifying column to be operated for the production of a (meth)acrylic ester.

This invention enjoys exceptionally high economic value in respect that it is capable of avoiding the possibility of explosion and combustion during the operation of stopping the purifying column and moreover preventing the polymerization.

EXAMPLES

Now, this invention will be described more specifically below by adducing working examples.

Example 1

A purifying column measuring 1500 mm in inside diameter and having incorporated therein 50 stepped sieve trays made of stainless steel (SUS 316) as shown FIG. 3 was used. It was provided in the top thereof with an output port and a reflux liquid inlet pipe, in the central part thereof with an inlet pipe for supply of a treating liquid as raw material, and in the bottom part thereof with a circulating pipe for the treating liquid, a delivery pipe to the next step, a liquid delivery pump, and a strainer. The column was provided in the bottom part thereof with a reboiler (shell-and-tube type) passing a fluid inside the tubes by spontaneous circulation.

The purifying column was stopped by the following method. As regards the conditions for purification during the normal operation, the liquid supplied was composed of 98 wt % of acrylic acid and 2 wt % of acrylic acid dimer, the top pressure of the column was 47 hPa, the reflux ratio, R/D, was 0.5, and the ratio of concentrations, F/B, was 5.

(a) The supply of the feed material was stopped.
(b) The supply of steam to the reboiler was stopped.
(c) The supply of the reflux liquid to the column was simultaneously stopped.
(d) The extraction of the bottom liquid B of the column and the supply of the polymerization inhibitor were stopped.
(e) The circulation of the liquid in the condenser and around the bottom of the column was stopped.
(f) Nitrogen was supplied at a temperature of 20° C. to the column through the top to adjust the inner pressure of the column at 700 hPa. The inner gas of the column was cooled at an average rate of 0.2° C./min by the supply of this nitrogen gas.
(g) Air was supplied the column instead of the nitrogen. The oxygen concentration in the column was found by computation to be 7.2 vol. %.
(h) The residual liquid in the column was recovered. The limit of oxygen concentration, when determined under the conditions of 100 kPa, 100° C., and 0 vol. % of moisture concentration, was found to be 9.5 vol. %. The concentration of the gas of easily polymerizing compound was 3.0 vol. % at that time.

(Results)

In the operation of the steps (a)–(h) mentioned above, the inner temperature of the column and the inner pressure of the column showed no sign of abnormality, the explosion and combustion could be avoided, and the operation could be stopped substantially stably. The cooling required about three hours. When the purifying column was stopped and the interior thereof was visually inspected, about 1 kg of polymer was detected in the bottom part of the column and on the trays. No polymer was detected as in the pump. In the reboiler, one of the total of 300 tubes was clogged. The polymer was removed by a cleansing operation. The results are shown in Table 1. The properties shown in Table 1 were rated on the following three-point scale.

○: The operation of stopping the purifying column had no problem, no polymer was formed within one hour of cooling, the reboiler was not clogged, and the residual liquid in the column could be recovered.

Δ: Though the operation was stopped safely, the cooling (within 30° C. of the ambient temperature) required not less than one hour, the total amount of polymer was less than 5 kg, and the residual liquid in the column could be recovered.

×: The stop of the operation was not stable, the total amount of polymer was not less than 5 kg, the interior of the reboiler incurred clogging, the reboiler could not be easily cleansed, the residual liquid in the column could not be recovered.

Example 2

The stop was effected by following the procedure of Example 1 while feeding the reflux liquid till the inner temperature of the column fell (to not higher than the bottom temperature of the column, not higher than 40° C.). In consequence of the supply of the reflux liquid, the column was cooled at an average rate of about 3° C./min. During the operation of stopping the purifying column, the inner temperature of the column and the inner pressure of the column showed no sign of abnormality, the flammable range could be avoided, and the operation could be stably stopped. The cooling time was 30 minutes. When the column was stopped and the interior of the column was visually inspected, no polymer was detected. The results are shown in Table 1.

Example 3

A purifying column measuring 1500 mm in inside diameter and having incorporated therein 50 stepped sieve trays made of stainless steel (SUS 316) as shown FIG. 3 was used. It was provided in the top thereof with an output port and a reflux liquid inlet pipe, in the central part thereof with an inlet pipe for supply of a treating liquid as raw material, and in the bottom part thereof with a circulating pipe for the treating liquid, a delivery pipe to the next step, a liquid delivery pump, and a strainer. The column was provided in the bottom part thereof with a reboiler (shell-and-tube type) passing a fluid inside the tubes by spontaneous circulation. Incidentally, the ambient temperature was 20° C. The purifying column was stopped by the following method. As regards the conditions for purification during the normal operation, the liquid supplied was composed of 50 wt % of acrylic acid and 50 wt % of methyl acrylate, the pressure at the top of the column was atmospheric pressure, the reflux ratio, R/D was 2, and the ratio of concentrations, F/B, was 1.5.

(a) The supply of the feed material was stopped.
(b) The supply of steam to the reboiler was stopped.
(c) The supply of the reflux liquid was simultaneously stopped.
(d) The extraction of the bottom liquid of the column and the supply of the polymerization inhibitor were stopped.
(e) The circulation of the liquid in the condenser and around the bottom of the column was stopped.
(f) An inert gas having a temperature of 20° C. and an oxygen concentration of 7 vol. % was supplied to effect the cooling of the interior of the column. The cooling proceeded at an average rate of about 0.3° C./min. The oxygen concentration in the column was found by measurement to be 7.0 vol. %.
(g) The residual liquid in the column was recovered. The limit of oxygen concentration, when measured under the conditions of 100 kPa, 100° C., and 0 vol. % of moisture concentration, was found to be 9.6 vol. %. The concentration of the gas of easily polymerizing compound at his time was found to be 2.8 vol. %.

(Results)

In the operation of the steps (a)–(g) mentioned above, the inner temperature of the column and the inner pressure of the column showed no sign of abnormality, the explosion and combustion could be avoided, and the operation could be stopped substantially stably. The cooling, however, required about three hours. When the purifying column was stopped and the interior thereof was visually inspected, about 0.5 kg of polymer was detected in the bottom part of the column and on the trays. No polymer was detected as in the reboiler and the pump. The polymer was removed by a cleansing operation. The results are shown in Table 1.

Comparative Example 1

The purifying column was stopped by injecting steam into the column in the place of the supply of the inert gas for the purpose of avoiding the flammable range, contrary example 1. During the operation of stopping the purifying column, the inner temperature of the column fell at an average rate of about 0.1° C./min and the pump was stopped after developing cavitation. A large amount of polymer was detected in the strainer. About 5 kg of polymer in the bottom, about 10 kg of polymer on the trays, and a large amount of polymer were detected. In the reboiler, 10 of the total of 300 tubes were found to be clogged. Though the polymer was removed by a cleansing operation, part of this polymer could not be easily removed with the detergent and, therefore, had to be removed by the use of a chipping hammer. The cavitation inflicted damage to the impellers. The results are shown in Table 1.

TABLE 1

|  | Example 1 | Example 2 | Example 3 | Comparative Example 1 |
|---|---|---|---|---|
| Stationary conditions | | | | |
| Press. at the top of column (hPa) | 47 | 47 | 1013 | 47 |
| Reflux ratio, R/D | 0.5 | 0.5 | 2 | 0.5 |
| Ratio of concentrations, F/B | 5 | 5 | 1.5 | 5 |
| Amount of raw material supplied (kg/h) | 3000 | 3000 | 5000 | 3000 |
| Total conc. of polymerization inhibitor in the column (wt. %) | 1 | 1 | 1 | 1 |
| Composition of raw material liquid (wt. %) | 98 of Acrylic acid & 2 of acrylic acid dimer | 98 of Acrylic acid & 2 of acrylic acid dimer | 50 of acrylic acid & 50 of methyl-acrylate | 98 of Acrylic acid & 2 of acrylic acid dimer |
| Conditions for stopping the purifying column | | | | |
| Final conc. of oxygen in column (vol. %) | 7.2 | 7.2 | 7 | — |
| Kind of gas supplied | $N_2$, Air | $N_2$, Air | 7 vol. % $O_2$ gas | Steam |
| Kind of feed liquid for cooling | — | Reflux liquid | — | — |
| Gradient of cooling temp. (° C/min) | 0.2 | about 3 | about 0.3 | about 0.1 |
| Cooling time (min) | about 180 | about 30 | about 180 | — |
| Recovery of residual liquid in column | possible | possible | possible | impossible |
| Flammable range | | | | |
| Limit of oxygen conc. (vol. %) | 9.5 | 9.5 | 9.6 | 9.5 |
| State of operation | | | | |
| Inner temperature of column/inner pressure of column | normal | normal | normal | cooling impediment |
| Presence of pump cavitation | none | none | none | occurrence |
| Others | none | none | none | stop of pump |
| Visual inspection of the interior of the column (polymer) | | | | |
| Bottom part of the column (kg) | about 1 kg | none | about 0.5 kg | about 5 kg |
| Trays | about 1 kg | none | about 0.5 kg | about 10 kg |
| Pump | none | none | none | much |
| Clogging of reboiler (tube number) | 1 | none | none | 10 |
| Others | none | none | none | difficult of washing |
| Total rating | Δ | ○ | Δ | X |

What is claimed is:

1. A method for stopping a purifying column handling an easily polymerizing compound-containing solution, comprising the steps of:

lowering an inner oxygen concentration of said column below a limit of oxygen concentration by supplying an inert gas to said column while the concentration of a gas of the easily polymerizing compound is in the range of 100% to a lower limit of the flammable range in volume % of the purifying column; and stopping supply of a raw material to the purifying column thereby causing the interior of the purifying column to revert to atmospheric pressure, wherein an interior of said column is further cooled at a rate in a range of 0.01 to 10° C./min.

2. A method according to claim 1, wherein said inert gas is a gas having an oxygen concentration below said limit or nitrogen gas.

3. A method according to claim 1, wherein nitrogen gas is supplied as said inert gas until at least 20 vol. % of a total inner volume of said column and then air is supplied to said column.

4. A method according to claim 1, wherein during the stopping step the interior of said column is cooled by the step of supplying said inert gas into the interior of said column or supplying a reflux liquid.

5. A method according to claim 4, wherein said reflux liquid contains a polymerization inhibitor.

6. A method according to claim 1, wherein said easily polymerizing compound is (meth)acrylic acid or an ester thereof.

* * * * *